United States Patent
Zagorii

(10) Patent No.: US 9,545,409 B2
(45) Date of Patent: Jan. 17, 2017

(54) USE OF 1-ADAMANTYLETHYLOXY-3-MORPHOLINO-2-PROPANOL OR PHARMACEUTICALLY ACCEPTABLE SALTS THEREOF IN PHARMACEUTICAL COMPOSITIONS AS A NEURORETINAL PROTECTOR

(71) Applicant: Gleb Vladimirovich Zagorii, Kiev (UA)

(72) Inventor: Gleb Vladimirovich Zagorii, Kiev (UA)

(*) Notice: Subject to any disclaimer, the term of this patent is extended or adjusted under 35 U.S.C. 154(b) by 0 days.

(21) Appl. No.: 14/433,443

(22) PCT Filed: Sep. 17, 2013

(86) PCT No.: PCT/UA2013/000106
§ 371 (c)(1),
(2) Date: Apr. 3, 2015

(87) PCT Pub. No.: WO2014/055054
PCT Pub. Date: Apr. 10, 2014

(65) Prior Publication Data
US 2015/0265623 A1   Sep. 24, 2015

(30) Foreign Application Priority Data

Oct. 5, 2012 (UA) .................... 2012 11512
Sep. 9, 2013 (UA) .................... 2013 10844

(51) Int. Cl.
*A61K 31/5375*   (2006.01)

(52) U.S. Cl.
CPC ................ *A61K 31/5375* (2013.01)

(58) Field of Classification Search
CPC .................................... A61K 31/5375
See application file for complete search history.

(56) References Cited

U.S. PATENT DOCUMENTS 9,333,207 B2 *   5/2016   Zagorii .............. A61K 31/5375

FOREIGN PATENT DOCUMENTS

| UA | 23451 C1 | 12/1999 |
| UA | 17476 U | 9/2006 |
| UA | 62779 U | 9/2011 |

OTHER PUBLICATIONS

Ademil-Darnitsa, Normativno-direktivnye dokumenty MOZ Ukrainy, Nomer registratsionnogo udostovereniia: UA/4845/01/01 on Jul. 26, 2006, retrieved from the internet <URL: http://modocs.kiev.ua/likiview.php?id=5132> on Mar. 16, 2015.
International Searching Authority, International Search Report for International Application No. PCT/UA2013/000106, Dec. 26, 2013, 9 pages, Federal Service for Intellectual Property, Russia.

* cited by examiner

*Primary Examiner* — Sreeni Padmanabhan
*Assistant Examiner* — Jody Karol
(74) *Attorney, Agent, or Firm* — Alston & Bird LLP

(57) ABSTRACT

The use of 1-adamantylethyloxy-3-morpholino-2-propanol, or pharmaceutically acceptable salts thereof, in a concentration range of from 3 to 100 mg/ml in pharmaceutical compositions for parenteral administration in the treatment of degenerative neuroretinal diseases of various geneses.

1 Claim, No Drawings

USE OF 1-ADAMANTYLETHYLOXY-3-MORPHOLINO-2-PROPANOL OR PHARMACEUTICALLY ACCEPTABLE SALTS THEREOF IN PHARMACEUTICAL COMPOSITIONS AS A NEURORETINAL PROTECTOR

This application is a national stage application, filed under 35 U.S.C. §371, of International Application No. PCT/UA2013/000106, filed Sep. 17, 2013, which claims priority to Ukrainian Application No. 2012 11512, filed Oct. 5, 2012, and Ukrainian Application No. 2013 10844, filed Sep. 9, 2013, the contents of all of which as are being hereby incorporated by reference in their entirety.

The invention relates to medicine and pharmacy and concerns a pharmaceutical composition for parenteral use comprising 1-adamantylethyloxy-3-morpholino-2-propanol or pharmaceutically acceptable salts thereof as a neuroretinoprotector which may be used in pharmaceutical compositions for parenteral use, within the concentration range of 3-100 mg/ml.

The pathology of the retina and optic nerve occupies the significant place among the causes of sight-disabled persons. According to modern ideas ischemia is one of main pathogenetic components and a trigger that causes the most severe diseases of the retina and optic nerve, such as central retinal artery occlusion, optic neuropathies, including glaucoma, at age-associated macular degeneration, myopic retinal degeneration etc.

However, existing agents for pharmacotherapy of said diseases such as vasoactive drugs (aminophylline, vinpocetine, nicotinic acid, and pentoxifylline), fibrinolytic agents and enzymes (fibrinolysin), anticoagulants (heparin), antiplatelet agents (acetylsalicylic acid), antihypoxants (etylmetylhydroxy pyridine succinate), nootropic agents (piracetam), calcium channel blockers (nimodipine, nifedipine), antioxidants, vitamin preparations and their complexes (emoxypine, vitamins A, C and B group), hormones and anabolic steroids, tissue therapy drugs, polypeptide bioregulators and others are not always sufficiently effective and may not fully protect or restore the structure and function of eye ischemic tissues. At the same time the presence of adverse effects in existing drugs often limit their use and give rise to various complications. That is, at present, from a prospective of evidence-based medicine, the world lack a neuroprotective reference product with proven efficacy for treatment of destructive degenerative diseases of the retina and optic nerve.

According to modern ideas for protection of the retina and optic nerve (neuroprotection) the use of adamantane derivatives, including memantine, may be the most encouraging and promising due to the ability to delay retinal cell death by binding NMDA with glutamate receptors leading to discontinuation of prolonged penetration of $Ca^{2+}$ ions having cytotoxic effect, inside them. This mechanism of injury is one of the leading in the development of many diseases of the eye, especially glaucoma. However, the clinical success may only be achieved by using the NMDA-receptor antagonist that selectively reduce their excessive activation as physiological activity of NMDA-receptor is required for normal retina functioning.

The basis for development of a pharmaceutical composition for parenteral use comprising the active substance 1-adamantylethyloxy-3-morpholino-2-propanol or pharmaceutically acceptable salts thereof within the concentration range of 3-100 mg/ml is that it has the properties of fast blocking/unblocking NMDA-receptors. This may indicate to the protective effect thereof on ischemic retina and optic nerve and makes it promising (as opposed to non-competitive NMDA-receptor blockers) and safer as neuroprotective product.

The task of claimed utility model is to make a pharmaceutical composition for parenteral use comprising the active substance 1-adamantylethyloxy-3-morpholino-2-propanol or pharmaceutically acceptable salts thereof within the concentration range of 3-100 mg/ml to improve pharmacotherapy of neuroprotective diseases of various geneses.

The proposed pharmaceutical composition may be used under occlusion of retina blood vessels, optic neuropathies including glaucoma, at age-associated macular degeneration, myopic retinal degeneration, diabetic and glaucoma retinopathy, eye circulatory disorders, degenerative diseases of retina and optic nerve including its atrophy and subatrophy, retinal detachment before and after surgery on the eye, as well as at various injuries thereof.

Example 1.

The experimental treatment of rats with ischemia-reperfusion eye model with pharmaceutical composition for parenteral use comprising the active substance 1-adamantyletyloksy-3-morpholino-2-propanol or pharmaceutically acceptable salts thereof within 96 hours of ischemia at doses of 3; 5; 10; 20 and 100 mg/kg reduces the number of apoptotic and necrotic cells in eye posterior part, and perivascular edema is attenuated in the retina and optic nerve, which provides the protection from the destructive effects of ischemia and reperfusion of all retina layers (photoreceptor, outer and inner nuclear, inner retinal, including ganglion, which is the most sensitive to ischemia. It evidences the appropriateness for use of proposed pharmaceutical composition under conditions of retina blood vessels occlusion, optic neuropathies including glaucoma, at age-associated macular degeneration, myopic retinal degeneration, diabetic and glaucoma retinopathy, eye blood supply disturbance, degenerative diseases of retina and optic nerve including its atrophy and subatrophy, retinal detachment before and after eye surgery as well as variety of eye injuries.

Experimental therapy of rats with ischemia-reperfusion eye model with pharmaceutical composition for parenteral use comprising the active substance 1-adamantylethyloxy-3-morpholino-2-propanol or pharmaceutically acceptable salts thereof within 96 hours of ischemia at doses of 3; 5; 10; 20 and 100 mg/kg promoted the normalization of disturbed indicators of acid-alkali balance, oxidative stress and energy metabolism in ischemic brain.

This demonstrates the appropriateness for use of proposed pharmaceutical composition at retina blood vessels occlusion, optic neuropathies including glaucomatous.

Experimental treatment of rats with ischemia-reperfusion eye model with pharmaceutical composition for parenteral use comprising the active substance 1 -adamantyle-tyloxy-3-morpholino-2-propanol or pharmaceutically acceptable salts thereof within 96 hours of ischemia at doses of 3; 5; 10: 20 and 100 mg/kg promoted the reduction in retinal manifestations of endothelial dysfunction and nitro-sating stress. This demonstrates the appropriateness for use of proposed pharmaceutical composition at retina blood vessels occlusions, optic neuropathies including glaucomatous, diabetic and glaucoma retinopathy, circulatory eye disorders and retinal detachment.

Experimental therapy of rats with ischemia-reper-fusion eye model with pharmaceutical composition for parenteral use comprising the active substance 1-adamantyl-ethyloxy-3-morpholino-2-propanol or pharmaceutically acceptable salts thereof within 96 hours of ischemia at doses of 3; 5: 10; 20 and 100 mg/kg promoted the normalization of disturbed indicators of acid-alkali balance, oxidative stress and energy metabolism in the retina. This demonstrates the appropriateness for use of proposed pharmaceutical composition at retina blood vessels occlusion, optic neuropathies including glaucomatous, diabetic and glaucoma retinopathy, circulatory eye disorders and retinal detachment before and after surgery on the eye, but also and at various injuries thereof.

Example 5. Studies in rats have found that the use of the pharmaceutical composition for parenteral use comprising the active substance 1-adamantylethyloxy-3-morpholino-2-propanol or pharmaceutically acceptable salts thereof at intravenous administration to rats at doses of 3; 5; 10; 20 and 100 mg/kg stimulates blood circulation in the central eye artery under conditions of its model ischemia-reperfusion.

The ability of the pharmaceutical composition for parenteral use comprising the active substance 1-adamantylethyloxy-3-morpholino-2-propanol or pharmaceutically acceptable salts thereof to improve eye blood circulation demonstrates the appropriateness of its use in retina blood vessels occlusion, optic neuropathies including glaucomatous, at age-associated macular degeneration, myopic retinal degeneration, diabetic and glaucoma retinopathy, eye circulatory disorders, degenerative diseases of the retina and optic nerve including its atrophy and subatrophy, retinal detachment before and after surgery on the eye, as well as and at various injuries thereof.

Thus, the results of the studies show that the active ingredient and pharmaceutical composition for parenteral use comprising the active substance 1-adamantylethyloxy-3-morpholino-2-propanol or pharmaceutically acceptable salts thereof within the concentration range of 3-100 mg/ml have expressed neuroprotective properties under the conditions of ischemic-hypoxic injury of retina and optic nerve. This gives grounds to their use in clinical practice under the conditions of retina blood vessels occlusion, optic neuropathies including glaucomatous, at age-associated macular degeneration, myopic retinal degeneration, diabetic and glaucoma retinopa-thy, eye circulatory disorders, degenerative diseases of retina and optic nerve including its atrophy and subatrophy, retinal detachment before and after surgery on the eye as well as various injuries thereof.

The invention claimed is:

1. A method of treating neuroretinal disease, the method comprising administering a pharmaceutical composition comprising about 3-100 mg/ml of 1-adamantylethyloxy-3-morpholino-2-propanol or pharmaceutically acceptable salts thereof to a patient by parenteral administration, wherein the patient is suffering from one or more of retina blood vessel occlusion, optic neuropathies, age-associated macular degeneration, myopic retinal degeneration, diabetic and glaucoma retinopathy, eye circulatory disorders, degenerative diseases of retina and optic nerve including atrophy and subatrophy, and retinal detachment before and after surgery on the eye.

* * * * *